United States Patent
Marion

(10) Patent No.: US 9,579,144 B2
(45) Date of Patent: *Feb. 28, 2017

(54) ELECTROSURGICAL SYSTEM AND METHOD HAVING ENHANCED TEMPERATURE MEASUREMENT

(71) Applicant: ArthroCare Corporation, Austin, TX (US)

(72) Inventor: Duane W. Marion, Santa Clara, CA (US)

(73) Assignee: ArthroCare Corporation, Austin, TX (US)

( * ) Notice: Subject to any disclaimer, the term of this patent is extended or adjusted under 35 U.S.C. 154(b) by 305 days.

This patent is subject to a terminal disclaimer.

(21) Appl. No.: 14/175,665

(22) Filed: Feb. 7, 2014

(65) Prior Publication Data

US 2014/0155884 A1 Jun. 5, 2014

Related U.S. Application Data

(63) Continuation of application No. 12/771,129, filed on Apr. 30, 2010, now Pat. No. 8,696,659.

(51) Int. Cl.
*A61B 18/12* (2006.01)
*A61B 18/14* (2006.01)
(Continued)

(52) U.S. Cl.
CPC ........ *A61B 18/1233* (2013.01); *A61B 18/148* (2013.01); *A61B 90/06* (2016.02);
(Continued)

(58) Field of Classification Search
CPC ......... A61B 18/04; A61B 18/08; A61B 18/10; A61B 18/12; A61B 18/1233; A61B 18/1266; A61B 18/14; A61B 18/1442; A61B 18/1445; A61B 18/1448; A61B 18/148; A61B 18/1492; A61B 2018/00011; A61B 2018/00702; A61B 2018/00744; A61B 2018/00767; A61B 2018/00791; A61B 2018/1472; A61B 2017/00084; A61B 2017/00088
(Continued)

(56) References Cited

U.S. PATENT DOCUMENTS

| | | | | |
|---|---|---|---|---|
| 5,653,692 A | * | 8/1997 | Masterson | A61B 18/08 604/113 |
| 2001/0001314 A1 | * | 5/2001 | Davison | A61B 18/1206 606/41 |

(Continued)

*Primary Examiner* — Michael Peffley
*Assistant Examiner* — Khadijeh Vahdat
(74) *Attorney, Agent, or Firm* — David A. Warmbold

(57) ABSTRACT

Electrosurgical systems and methods are described herein in which the temperature of a fluid within a body or joint space is determined and/or monitored despite the energy generated during treatment by an ablation probe. One or more temperature sensors are positioned along the probe proximally of the electrode assembly and measure the temperature of an electrically conductive fluid without being overly influenced by the surgical effect occurring proximate the electrode assembly. A controller automatically suspends energy delivery for one or more periods of time while the temperature is monitored.

20 Claims, 11 Drawing Sheets

(51) Int. Cl.
*A61B 17/00* (2006.01)
*A61B 18/00* (2006.01)

(52) U.S. Cl.
CPC ........... *A61B 2017/00084* (2013.01); *A61B 2017/00088* (2013.01); *A61B 2018/00011* (2013.01); *A61B 2018/00702* (2013.01); *A61B 2018/00744* (2013.01); *A61B 2018/00767* (2013.01); *A61B 2018/00791* (2013.01); *A61B 2018/1472* (2013.01); *A61B 2218/007* (2013.01)

(58) Field of Classification Search
USPC .................................................. 606/33–50
See application file for complete search history.

(56) References Cited

U.S. PATENT DOCUMENTS

| | | | | |
|---|---|---|---|---|
| 2002/0026127 | A1* | 2/2002 | Balbierz | A61B 18/1206 600/567 |
| 2003/0088245 | A1* | 5/2003 | Woloszko | A61B 18/148 606/41 |
| 2003/0097129 | A1* | 5/2003 | Davison | A61B 18/14 606/41 |

\* cited by examiner

TIME (t)

ELECTROSURGICAL SYSTEM AND METHOD HAVING ENHANCED TEMPERATURE MEASUREMENT

CROSS-REFERENCE TO RELATED APPLICATIONS

This application is a continuation of U.S. patent application Ser. No. 12/771,129 filed Apr. 30, 2010, now U.S. Pat. No. 8,696,659, the complete disclosure of which is incorporated herein by reference for all purposes.

FIELD OF THE INVENTION

The present invention relates to systems and methods for measuring temperatures during electrosurgical procedures within a body space of a patient body, such as within a joint. More particularly, the present invention relates to methods and apparatus for measuring temperatures of an electrically conductive fluid within a body space during ablation, such as within a joint space, without being significantly influenced by the surgical effect initiated at the active electrode.

BACKGROUND OF THE INVENTION

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on a separate electrode for the return of RF current, that is placed away from the surgical site on the body of the patient, and where the surgical device defines only a single electrode pole that provides the surgical effect. Bipolar devices comprise both electrodes for the application of current between their surfaces.

Electrosurgical procedures and techniques are particularly advantageous since they generally reduce patient bleeding and trauma associated with cutting operations. Additionally, electrosurgical ablation procedures, where tissue surfaces and volume may be reshaped, cannot be duplicated through other treatment modalities.

Present electrosurgical techniques used for tissue ablation suffer from an inability to control the depth of necrosis in the tissue being treated. Most electrosurgical devices rely on creation of an electric arc between the treating electrode and the tissue being cut or ablated to cause the desired localized heating. Such arcs, however, often create very high temperatures causing a depth of necrosis greater than 500 µm, frequently greater than 800 µm, and sometimes as great as 1700 µm. The inability to control such depth of necrosis is a significant disadvantage in using electrosurgical techniques for tissue ablation, particularly in arthroscopic procedures for ablating and/or reshaping fibrocartilage, articular cartilage, meniscal tissue, and the like.

Generally, radiofrequency (RF) energy is extensively used during arthroscopic procedures because it provides efficient tissue resection and coagulation and relatively easy access to the target tissues through a portal or cannula. However, a typical phenomenon associated with the use of RF during these procedures is that the currents used to induce the surgical effect can result in heating of electrically conductive fluid used during the procedure to provide for the ablation and/or to irrigate the treatment site. If the temperature of this fluid were allowed to increase above a threshold temperature value, the heated fluid could result in undesired necrosis or damage to surrounding neuromuscular and/or soft tissue structures.

Previous attempts to mitigate these damaging effects have included either limiting the power output of the RF generator or to include a suction lumen on the distal tip of the electrosurgical device to continuously remove the affected fluid from the surgical site and thereby reduce the overall temperature. These solutions may be effective but are limited and they do not allow for direct feedback based upon the actual temperature of the fluid within the joint space. Furthermore, limiting the power output of the generator reduces the rate of the surgical effect, which is often unacceptable from a clinical perspective. The incorporation of a suction lumen to allow heated fluid to be removed also reduces the performance of the electrosurgical device.

There have been numerous RF based systems introduced into the market that make use of a temperature sensor (e.g., a thermocouple) in order to monitor the temperature of tissue at or near the electrode.

However, the temperature sensors are susceptible to electrical noise. Electrical noise may arise from a number of sources including, for example, (1) high frequency noise present on the electrical circuit used to measure the small voltages induced by the temperature sensor, namely, a thermocouple, or (2) resistive heating of the thermocouple junction arising from the delivery of the ablative energy to the tissue.

Filtering the measured signal to reject the high frequency components can generally remove the high frequency noise described above. However, the error arising from the resistive heating of the thermocouple junction is a physical phenomena that cannot be mitigated by filtering. An improved system and method to accurately monitor the temperature of the fluid is still desired.

SUMMARY OF THE INVENTION

During the electrosurgical ablation of tissue wherein an electrosurgical probe comprising a temperature sensor is positioned in electrically conductive fluid in the region of the target tissue, a controller is operative to receive a temperature signal from the temperature sensor positioned in the electrically conductive fluid. The controller is further operable to automatically suspend or reduce delivery of the high frequency energy to the active electrode terminal of the probe for one or more suspension periods. The controller monitors the temperature signal during the suspension periods. The temperature of the electrically conductive fluid at the target site is calculated or estimated by the controller based on the monitored temperature signal. During the suspension period, and while the energy is suspended or substantially lowered, the temperature signal stabilizes thereby enhancing temperature measurement.

The duration of the suspension period may be fixed, or varied and based on feedback from the procedure. In one embodiment the suspension period continues until the change in temperature is less than a threshold value. In another embodiment the suspension period is fixed at a value equal to or greater than 250 ms.

In another embodiment, the controller is operable to suspend delivery of high frequency energy for a plurality of suspension periods. The plurality of suspension periods are determined by the controller according to a suspension frequency (F) equal to the number of suspension periods per second. The suspension frequency (F) may be calculated or set by the controller using one or more techniques or algorithms. In one embodiment the controller is adapted to receive an input corresponding to a surgical procedure and the suspension frequency (F) is determined based on said input. In another embodiment the suspension frequency (F) is based on a power output. In another embodiment the suspension frequency (F) is based on the measured temperature and is increased when the measured temperature reaches a threshold temperature. Typically, the frequency (F) of temperature-monitoring periods shall be between ⅓ and 2.

In another embodiment, the controller includes a means to detachably and electrically couple with the electrosurgical probe. This may be in the form of an input jack, or receptacle. In another embodiment the controller includes a microprocessor for controlling the power supply and an analog-to-digital converter for converting the temperature signal to a digital signal readable by the microprocessor.

In another embodiment the system includes the electrosurgical probe and the probe comprises one or more fluid delivery and/or aspiration elements. The fluid delivery element directs fluid to the target site. The fluid delivery element is coupled to a pump which is operable to control fluid inflow to the target site. The controller is operable to control the pump and the fluid inflow in order to maintain the temperature of the fluid below a predetermined level. The system may also include a fluid aspiration lumen wherein the fluid aspiration lumen is a component of the electrosurgical probe.

In another embodiment, a method for ablating tissue at a target site comprises positioning a distal end of an electrosurgical instrument adjacent to the tissue to be treated. High frequency energy is applied by the instrument. The method further includes sensing a temperature of the electrically conductive fluid in the vicinity of the tissue and automatically adjusting or suspending the step of applying the high frequency energy while continuing to sense the temperature. Adjusting the energy delivery may be performed by, for example, substantially lowering or suspending the delivery of energy.

In the step of suspending applying high frequency energy, the duration of the suspension period may be fixed, vary, or based on feedback from the procedure. In one embodiment the suspension period continues until the change in temperature is less than a threshold value. In another embodiment the suspension period is fixed at a value equal to or greater than 250 ms.

In another embodiment, the step of suspending comprises suspending the applying step for plurality of suspension periods according to a suspension frequency (F). The suspension frequency (F) is at least 1 period every 3 seconds and less than 2 periods per second.

In another embodiment, the suspension frequency (F) is determined based on power output. In another embodiment, the suspension frequency (F) is determined based on receiving an input of a type of surgical procedure to be performed. In another embodiment, the suspension frequency (F) is determined based on sensing the temperature, and the suspension frequency (F) is increased once the temperature reaches a threshold limit.

The method may further include a step of circulating fluid to the target site at a flowrate adjusted by the controller. The measured temperature is compared to a desired temperature range and the flowrate is adjusted based on the measured temperature.

In another embodiment, the applying step forms a plasma in the vicinity of the active electrode terminal of the electrosurgical probe thereby causing ablation of the soft tissue.

In another embodiment, the method is performed wherein the target site is a joint.

The description, objects and advantages of the present invention will become apparent from the detailed description to follow, together with the accompanying drawings.

DETAILED DESCRIPTION OF THE INVENTION

Figure 1:
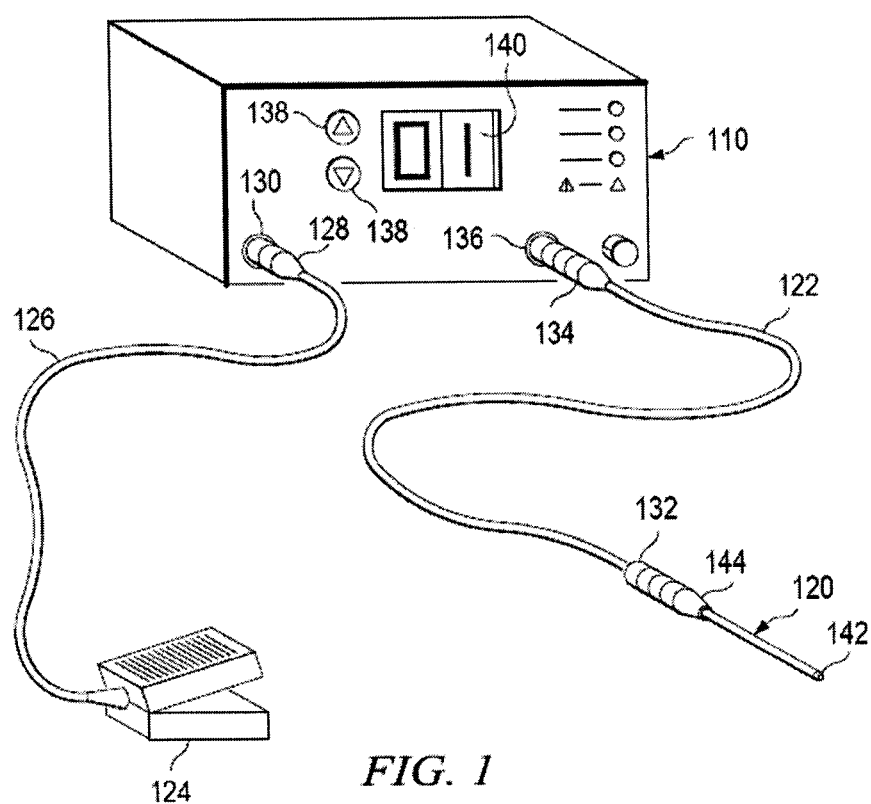
FIG. 1 is a perspective view of the electrosurgical system including an electrosurgical probe and electrosurgical power supply.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The treatment device of the present invention may have a variety of configurations. However, one variation of the device employs a treatment device using Coblation® technology.

The assignee of the present invention developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) and in the region between the tip of the active electrode(s) and the target tissue. The electrically conductive fluid may be a liquid or gas, such as isotonic saline, blood, extracellular or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm3 for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882 the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in commonly assigned U.S. Pat. Nos. 6,355,032; 6,149,120 and 6,296,136, the complete disclosures of which are incorporated herein by reference.

The active electrode(s) of a Coblation® device may be supported within or by an inorganic insulating support positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

In one example of a Coblation® device for use with the embodiments disclosed herein, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

A Coblation® treatment device for use according to the present embodiments may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation® device is not limited to electrically isolated active electrodes, or even to a plurality of active electrodes. For example, the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation.)

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source may deliver a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly frequencies around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 µH to 50,000 µH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

Moreover, other treatment modalities (e.g., laser, chemical, other RF devices, etc.) may be used in the inventive method either in place of the Coblation® technology or in addition thereto.

Referring now to FIG. 1, an exemplary electrosurgical system for resection, ablation, coagulation and/or contraction of tissue will now be described in detail. As shown, certain embodiments of the electrosurgical system generally include an electrosurgical probe 120 connected to a power supply 110 for providing high frequency voltage to one or more electrode terminals on probe 120. Probe 120 includes a connector housing 144 at its proximal end, which can be removably connected to a probe receptacle 132 of a probe cable 122. The proximal portion of cable 122 has a connector 134 to couple probe 120 to power supply 110 at receptacle 136. Power supply 110 has an operator controllable voltage level adjustment 138 to change the applied voltage level, which is observable at a voltage level display 140. Power supply 110 also includes one or more foot pedals 124 and a cable 126 which is removably coupled to a receptacle 130 with a cable connector 128. The foot pedal 124 may also include a second pedal (not shown) for remotely adjusting the energy level applied to electrode terminals 142, and a third pedal (also not shown) for switching between an ablation mode and a coagulation mode.

Figure 2:
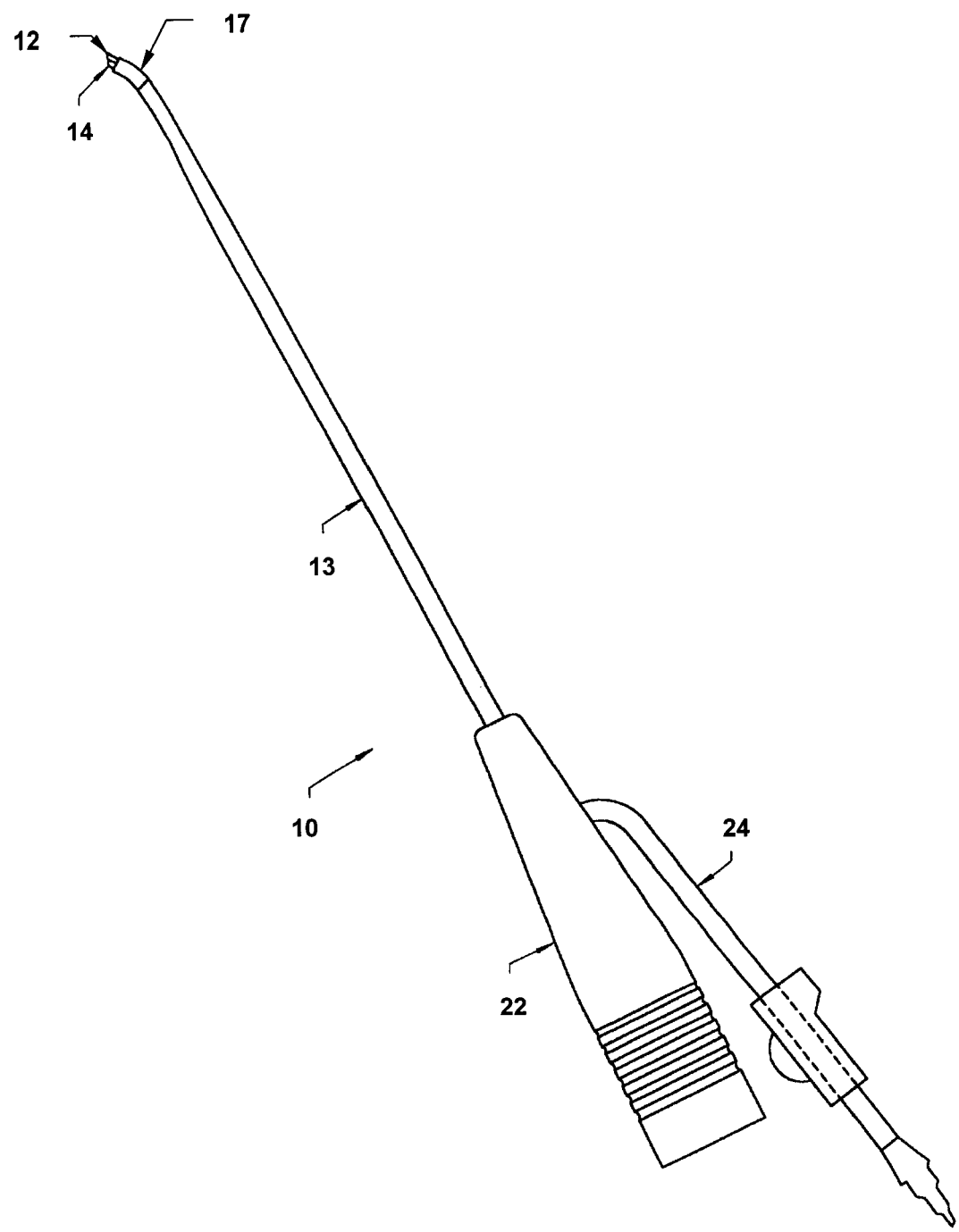
FIG. 2 is side view of an electrosurgical probe according to the present embodiments.

Referring now to FIG. 2, an electrosurgical probe 10 representative of the currently described embodiments includes an elongate shaft 13 which may be flexible or rigid, a handle 22 coupled to the proximal end of shaft 13 and an electrode support member 14 coupled to the distal end of shaft 13. Probe 10 includes an active electrode terminal 12 disposed on the distal tip of shaft 13. Active electrode 12 may be connected to an active or passive control network within a power supply and controller 110 (see FIG. 1) by means of one or more insulated electrical connectors (not shown). The active electrode 12 is electrically isolated from a common or return electrode 17 which is disposed on the shaft proximally of the active electrode 12, preferably being within 1 mm to 25 mm of the distal tip. Proximally from the distal tip, the return electrode 17 is generally concentric with the shaft of the probe 10. The support member 14 is positioned distal to the return electrode 17 and may be composed of an electrically insulating material such as epoxy, plastic, ceramic, glass or the like. Support member 14 extends from the distal end of shaft 13 (usually about 1 to 20 mm) and provides support for active electrode 12.

Figure 3:
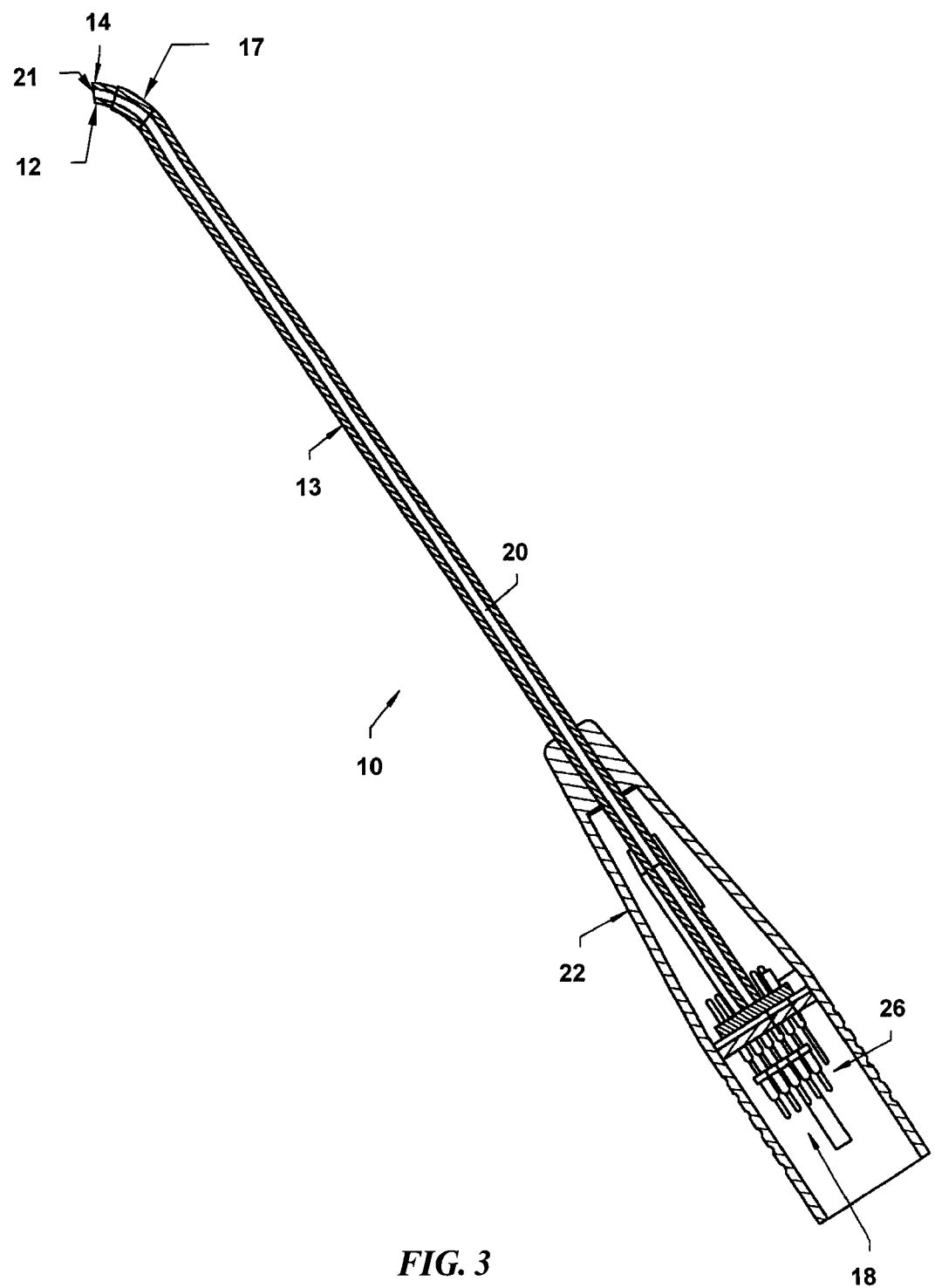
FIG. 3 is a cross-sectional view of the electrosurgical probe of FIG. 2.

Referring now to FIG. 3, probe 10 may further include a suction lumen 20 for aspirating excess fluids, bubbles, tissue fragments, and/or products of ablation from the target site. Suction lumen 20 extends through support member 14 to a distal opening 21, and extends through shaft 13 and handle 22 to an external connector 24 (see FIG. 2) for coupling to a vacuum source. Typically, the vacuum source is a standard hospital pump that provides suction pressure to connector 24 and suction lumen 20. Handle 22 defines an inner cavity 18 that houses electrical connections 26 and provides a suitable interface for electrical connection to power supply/controller 110 via an electrical connecting cable 122 (see FIG. 1).

In certain embodiments, active electrode 12 may comprise an active screen electrode 40. Screen electrode 40 may have a variety of different shapes, such as the shapes shown in FIGS. 4A and 4B. Electrical connectors 48 (see FIG. 9) extend from connections 26 through shaft 13 to screen electrode 40 to electrically couple the active screen electrode 40 to the high frequency power supply 110 (see FIG. 1). Screen electrode 40 may comprise a conductive material, such as tungsten, titanium, molybdenum, platinum, or the like. Screen electrode 40 may have a diameter in the range of about 0.5 to 8 mm, preferably about 1 to 4 mm, and a thickness of about 0.05 to about 2.5 mm, preferably about 0.1 to 1 mm. Screen electrode 40 may comprise a plurality of apertures 42 configured to rest over the distal opening 21 of suction lumen 20. Apertures 42 are designed to allow for the passage of aspirated excess fluids, bubbles, and gases from the ablation site and are typically large enough to allow ablated tissue fragments to pass through into suction lumen 20. As shown, screen electrode 40 has a generally irregular shape which increases the edge to surface-area ratio of the screen electrode 40. A large edge to surface-area ratio increases the ability of screen electrode 40 to initiate and maintain a plasma layer in conductive fluid because the edges generate higher current densities, which a large surface area electrode tends to dissipate power into the conductive media.

Figure 4A:
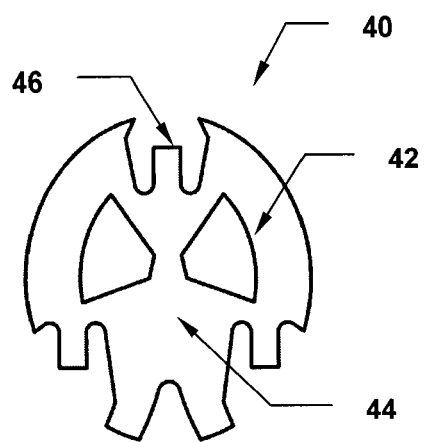
FIG. 4A is a perspective view of an embodiment of the active electrode for the probe of FIGS. 1 and 2.
Figure 4B:
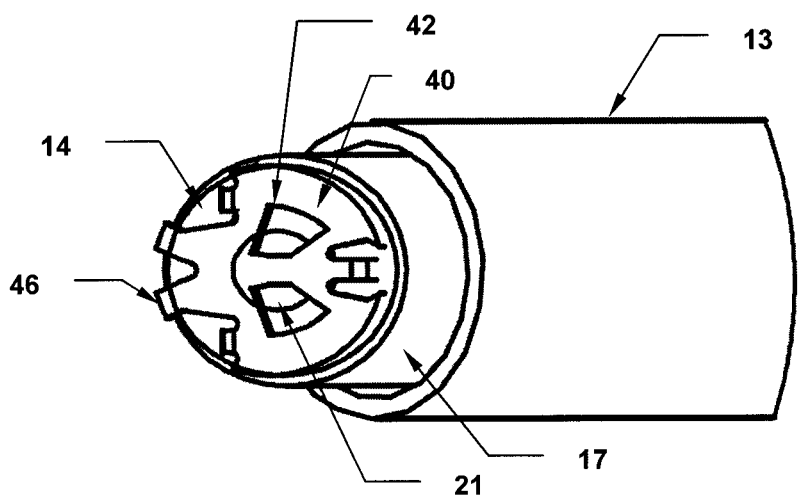
FIG. 4B is a detailed view of the distal tip of the electrosurgical probe of FIGS. 1 and 2 incorporating the active screen electrode of FIG. 4A.

In the representative embodiment shown in FIGS. 4A and 4B, screen electrode 40 includes a body 44 that rests over insulative support member 14 and the distal opening 21 to suction lumen 20. Screen electrode 40 further comprises at least five tabs 46 that may rest on, be secured to, and/or be embedded in insulative support member 14. In certain embodiments, electrical connectors 48 (see FIG. 9) extend through insulative support member 14 and are coupled (i.e., via adhesive, braze, weld, or the like) to one or more of tabs 46 in order to secure screen electrode 40 to the insulative support member 14 and to electrically couple screen electrode 40 to power supply 110 (see FIG. 1). Preferably, screen electrode 40 forms a substantially planar tissue treatment surface for smooth resection, ablation, and sculpting of the meniscus, cartilage, and other soft tissues. In reshaping cartilage and meniscus, the physician often desires to smooth the irregular, ragged surface of the tissue, leaving behind a substantially smooth surface. For these applications, a substantially planar screen electrode treatment surface is preferred.

Further details and examples of instruments which may be utilized herein are described in detail in U.S. Pat. Nos. 6,254,600; 6,557,559 and 7,241,293 which are incorporated herein by reference in their entirety.

Figure 5:
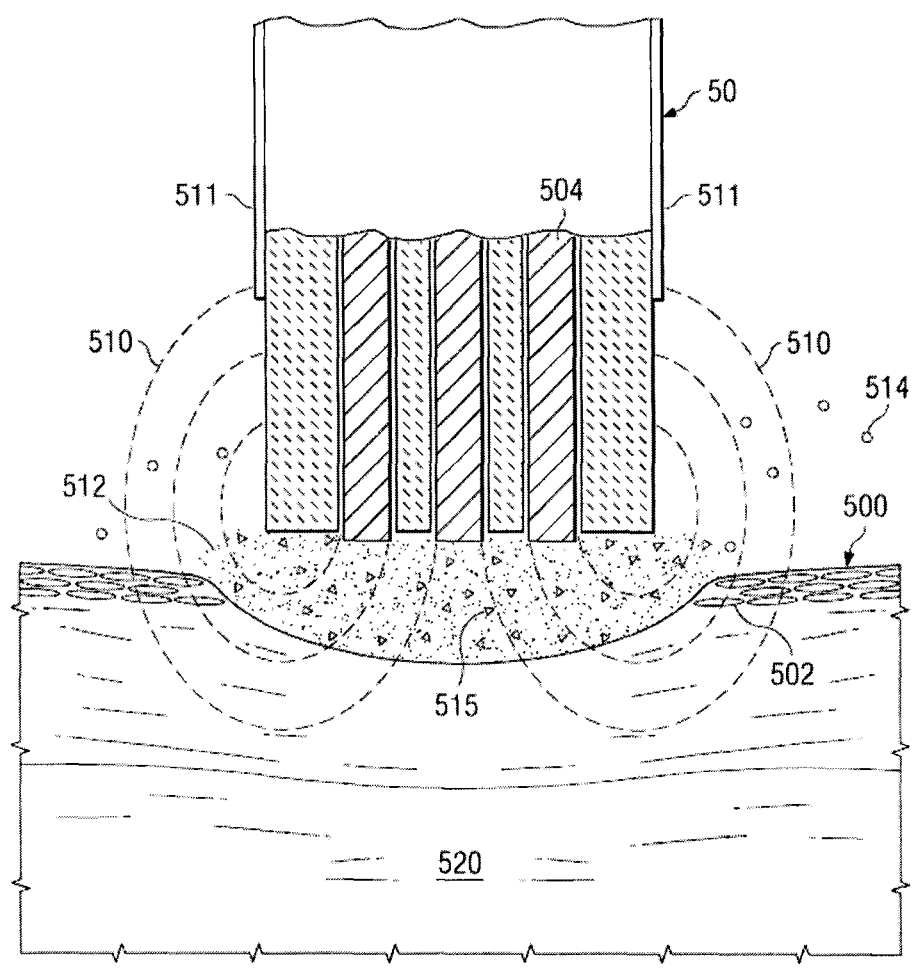
FIG. 5 illustrates a detailed view illustrating ablation of tissue.

FIG. 5 representatively illustrates in more detail the removal of a target tissue by use of an embodiment of a representative electrosurgical probe 50 according to the present disclosure. As shown, the high frequency voltage is sufficient to convert the electrically conductive fluid (not shown) between the target tissue 502 and active electrode terminal(s) 504 into an ionized vapor layer 512 or plasma. As a result of the applied voltage difference between electrode terminal(s) 504 and the target tissue 502 (i.e., the voltage gradient across the plasma layer 512), charged particles 515 in the plasma are accelerated. At sufficiently high voltage differences, these charged particles 515 gain sufficient energy to cause dissociation of the molecular bonds within tissue structures in contact with the plasma field. This molecular dissociation is accompanied by the volumetric removal (i.e., ablative sublimation) of tissue and the production of low molecular weight gases 514, such as oxygen, nitrogen, carbon dioxide, hydrogen and methane. The short range of the accelerated charged particles 515 within the tissue confines the molecular dissociation process to the surface layer to minimize damage and necrosis to the underlying tissue 520.

During the process, the gases 514 will be aspirated through a suction opening and suction lumen to a vacuum source (not shown). In addition, excess electrically conductive fluid, and other fluids (e.g., blood) will be aspirated from the target site 500 to facilitate the surgeon's view. During ablation of the tissue, the residual heat generated by the current flux lines 510 (typically less than 150° C.) between electrode terminals 504 and return electrode 511 will usually be sufficient to coagulate any severed blood vessels at the site. If not, the surgeon may switch the power supply (not shown) into the coagulation mode by lowering the voltage to a level below the threshold for fluid vaporization, as discussed above. This simultaneous hemostasis results in less bleeding and facilitates the surgeon's ability to perform the procedure.

Figure 6A:
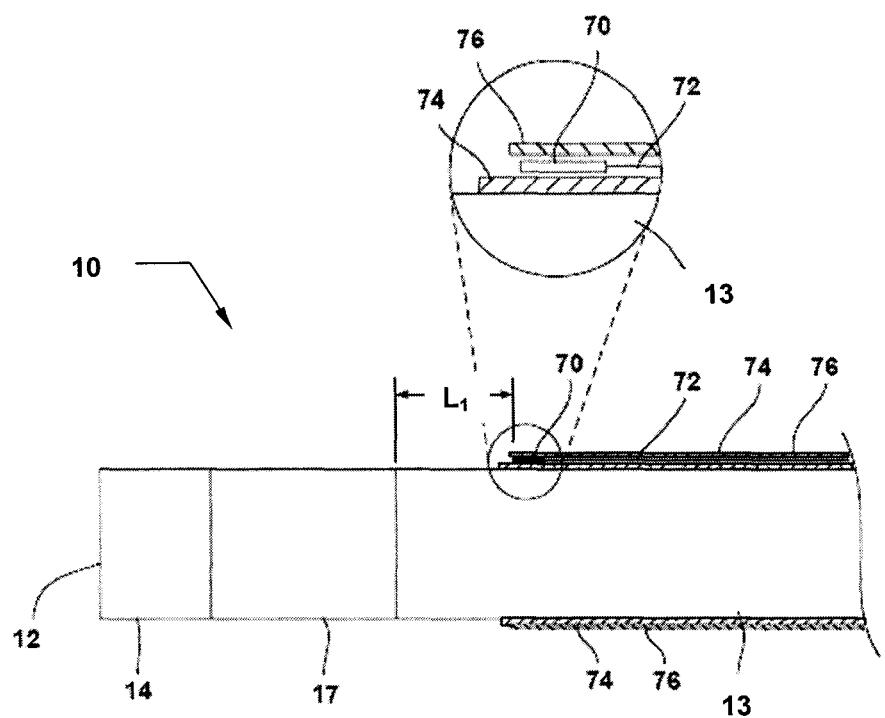
FIG. 6A is a partial cross-sectional side view of a temperature sensor positioned along the shaft of an electrosurgical probe proximally of the electrode assembly.

Because of the energy generated and applied during treatment within the patient body with the above-described probe 10 or other variations thereof, difficulties arise in determining, monitoring, and/or limiting the actual temperature of electrically conductive fluid irrigating the treated body space, joint, or tissue region. Accordingly, probe 10 may include mechanisms for measuring a temperature of the electrically conductive fluid itself without being overly influenced by the surgical effect occurring at the active electrode 12. Turning to FIG. 6A, one embodiment is illustrated in the side view of probe 10 and the detail side view showing a temperature sensor 70 positioned along the probe shaft proximally of the return electrode 17. Temperature sensor 70 may comprise any number of sensors, e.g., thermocouple, thermistor, resistance temperature detector (RTD), etc. In particular, temperature sensor 70 may comprise a T-type thermocouple as these sensors are well-established for use in such probes.

To reduce or eliminate the temperature-monitoring influence from an active electrode 12 during tissue treatment, sensor 70 is desirably distanced from both the active electrode 12 and return electrode 17 and may accordingly be positioned proximally along the shaft 13 of probe 10. In the example shown, the distance $L_1$ of sensor 70 removed from return electrode 17 is at least 5 mm but may also be less than or greater than this distance, as practicable. With sensor 70 positioned accordingly, the sensor 70 may measure the temperature of the infused electrically conductive fluid/irrigant surrounding the probe 10 and sensor 70 as the temperature of the fluid is indicative of the temperature of the surrounding tissue or joint space within which probe 10 may be positioned for treatment. The fluid temperature may thus be measured without regard to any energy generated by the current traveling between active electrode 12 and return electrode 17 of probe 10.

A method to improve temperature measurement and reduce noise includes adjusting (e.g., lowering or suspending) energy delivery for one or more periods of time while continuing to monitor the temperature signal. This may be performed, for example, using a controller 110 as shown and described in FIG. 10.

The controller determines the period of time that the RF energy is suspended. The period of time is preferably sufficient for the noise to diminish, and for the temperature measurement to stabilize. In one embodiment, the suspension period is set at a constant value equal to or greater than 100 ms, and more preferably equal to or greater than 250 ms.

The suspension period may also be determined as a function of time. The controller allows or permits the suspension period to continue until the temperature varies less than about 1 degree per 50 ms.

In one embodiment of the invention, the frequency (F) of the suspension periods (e.g., the number of periods per second) is determined by the controller. The frequency (F) may be a predetermined constant value. This value may be selected or programmed conservatively at, for example, 2 periods per second or more.

In another embodiment, the controller operates to determine the frequency of the suspension periods (F) based on the magnitude and/or variability of the temperature, or the power output measured in real time during a procedure. For example, in one embodiment of the invention, at high temperatures or power outputs the controller operates to increase the frequency of the suspension periods so that safety of the patient is not compromised. Similarly, when the temperature varies greatly, the controller operates to increase the frequency of both the temperature measurement and the suspension periods.

In another embodiment, the controller is programmed to receive an input signal from an operator corresponding to a type of procedure to be performed. The controller determines the frequency (F) of the suspension periods based on the type of procedure. For example, a procedure requiring coagulation would typically be associated with higher heat generation. The controller would thus increase the frequency of suspension periods or temperature-monitoring periods to increase the accuracy and safety of the procedure. Should a temperature of the electrically conductive fluid exceed a threshold temperature, the system would make adjustments to the power output or another component of the system in order to reduce the measured temperature.

In another embodiment, the controller includes a database containing a plurality of types of procedures, and a frequency and suspension period corresponding to each type of procedure. The controller receives an input procedure signal and automatically determines the frequency and suspension period according to a predetermined value from the database.

The above described frequency (F) typically is between one period every 500 ms to one period every 3000 ms. However, the invention is not intended to be limited as such except as where specifically stated in the appended claims.

Figure 15:
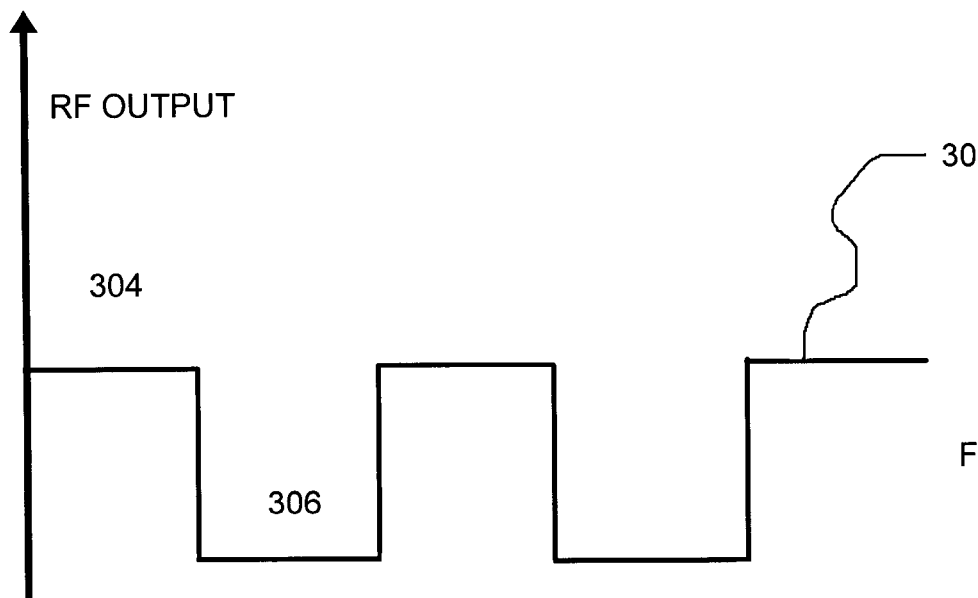
FIG. 15 is an illustrative graph showing energy output versus time.
Figure 16:
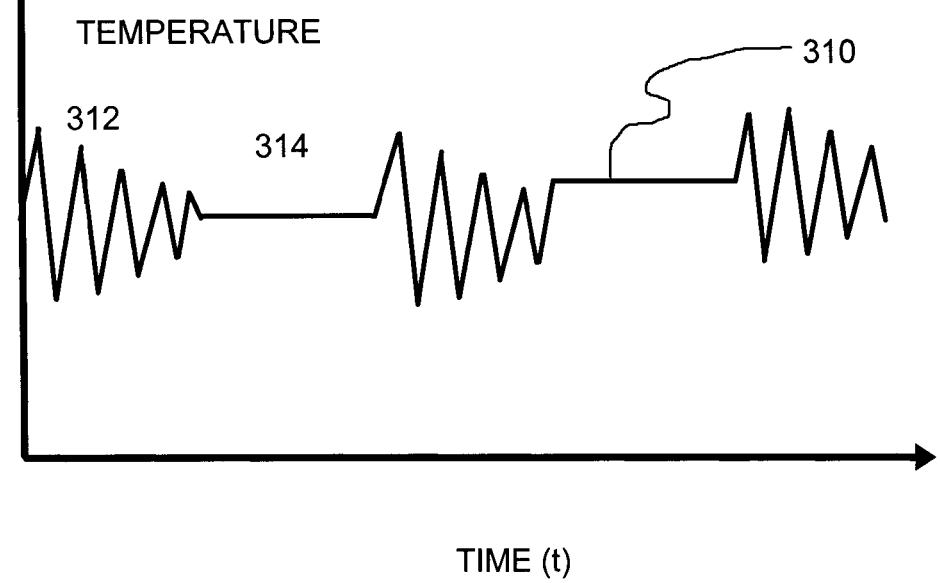
FIG. 16 is an illustrative graph showing temperature versus time.

FIGS. 15-16 illustrate a graphical representation of the application of energy and temperature versus time. FIG. 15 shows an RF output curve 300 representative of the application of voltage or RF output in bursts or pulses. The energy is applied for a period of time (e.g., an active period 304) and suspended for a period of time (suspension period 306). Curve 300 shows a plurality of suspension periods.

FIG. 16 shows an illustration of a temperature curve 310 including a plurality of noise areas 312 and noise-free areas 314. The noise areas and noise-free areas correspond to the active periods and suspension periods of FIG. 15 respectively.

As shown, the temperature stabilizes during the suspension periods 314. In contrast, during energy delivery periods 304 the temperature fluctuates greatly illustrating the benefits of periodically suspending application of energy while monitoring the temperature.

Temperature sensor 70 may be mounted directly upon the shaft as illustrated in FIG. 6A. However, certain embodiments of probe 10 may have a suction lumen (see FIG. 3) for aspirating fluid and ablative byproducts from the treatment site, wherein the inflow and/or outflow of fluid and gas through the underlying suction lumen may affect the temperature sensed by sensor 70. Thus, a thermally insulative layer 74 such as heat shrink tubing or other insulation (e.g., comprised of thermoplastics, such as polyolefin, polyvinyl chloride (PVC), polytetrafluoroethylene (PTFE), fluorinated ethylene propylene (FEP), etc.) may be placed between the temperature sensor 70 and outer surface of shaft 13. Sensor 70 may be secured directly to the shaft 13 and/or underlying layer 74 via another insulative layer 76 overlying sensor 70 and conducting wire 72 coupled to sensor 70. This overlying insulative layer prevents the temperature of the surrounding fluid from effecting the measurement at sensor 70. The addition of the overlying layer 76, which may be comprised of any of the materials mentioned above, may also electrically isolate temperature sensor 70 from its surrounding saline environment to prevent or inhibit electrical noise from being introduced into the temperature measurement circuit. Overlying layer 76 may be adhesive lined to further isolate the sensor 70.

Figure 6B:
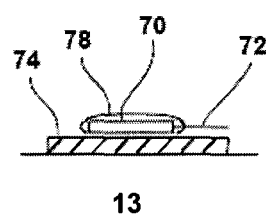
FIG. 6B is a detail cross-sectional side view of a temperature sensor insulated via an adhesive.

Additionally and/or alternatively, temperature sensor 70 may be isolated and secured to the underlying layer 74 by an adhesive 78, e.g., epoxy or cyanoacrylate glue, which may be adhered directly upon sensor 70, as illustrated in the detail side view of FIG. 6B.

Figure 7:
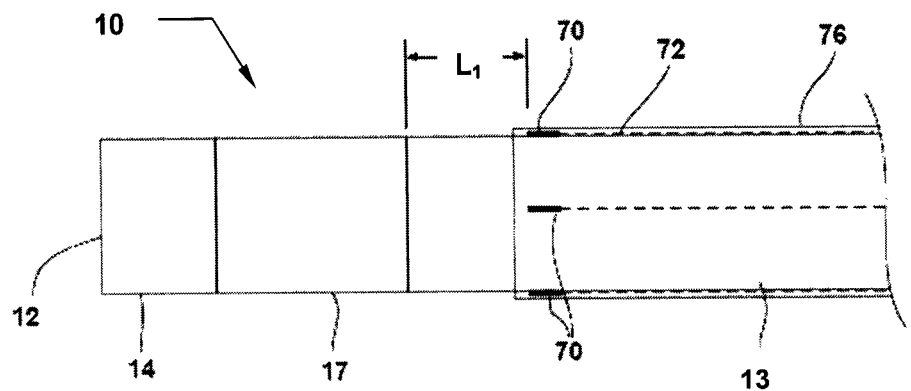
FIG. 7 is a side view of another variation where multiple temperature sensors may be positioned about the shaft of an electrosurgical probe proximally of the electrode assembly.

In another embodiment, a side view of FIG. 7 shows a variation where multiple temperature sensors 70, e.g., greater than one sensor, may be positioned around the shaft 13 to obtain multiple readings of the fluid temperature. Although the multiple temperature sensors 70 may be uniformly positioned relative to one another about a circumference of shaft 13, they may be alternatively positioned at arbitrary locations as well. Moreover, each of the multiple sensors 70 may be positioned at differing distances $L_1$ along shaft 13 from return electrode 17. In sensing the multiple fluid temperatures, each of the temperatures may be displayed to the user and/or alternatively they may be calculated to present an average temperature value to the user and/or the maximum of the measured values may be displayed.

Figure 8:
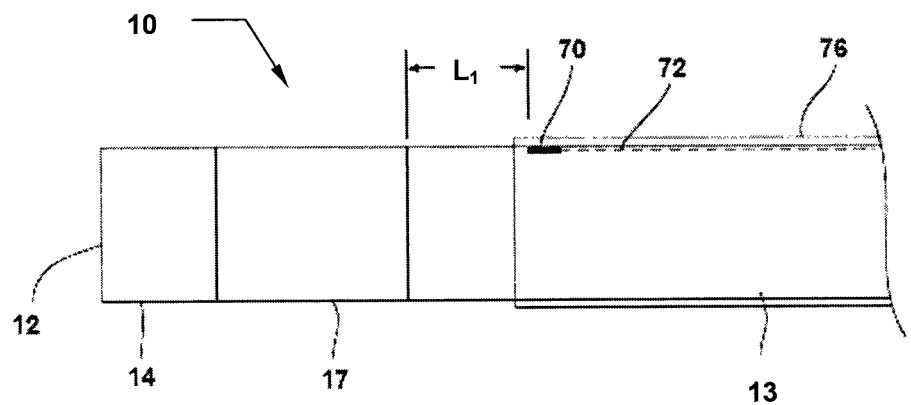
FIG. 8 is a side view of yet another variation in which a temperature sensor may be integrated along the shaft of an electrosurgical probe.

In yet another variation, a side view of FIG. 8 shows another variation where temperature sensor 70 may be integrated along the shaft 13 such that sensor 70 may be recessed along the shaft surface and conducting wire 72 may be passed through a lumen (not shown) defined through probe 10. Sensor 70 may still be insulated from the shaft 13 and may also be insulated as described above. In such an embodiment, a hole through shaft 13 may be located at the location of sensor 70 to improve the accuracy of the measurement of the fluid external to shaft 13.

Figure 9:
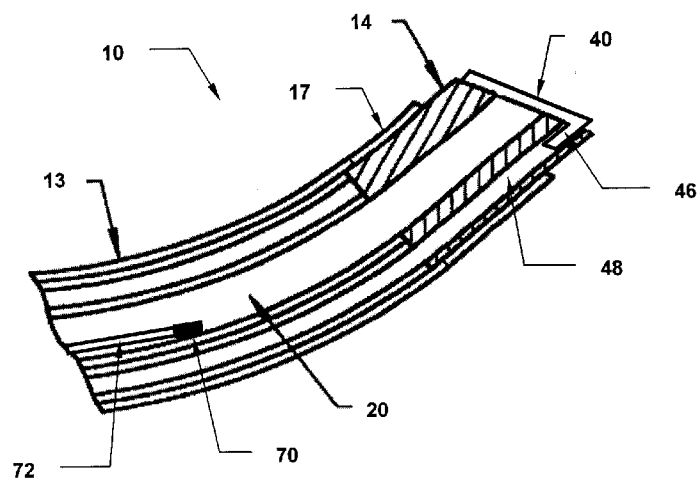
FIG. 9 is a side view of yet another variation where a temperature sensor may be positioned within a fluid lumen of an electrosurgical probe to sense the fluid temperature immediately removed from the vicinity of the active electrode.

Referring now to FIG. 9, in yet another variation a representative probe 10 having a suction lumen 20 for aspirating electrically conductive fluid from the body or joint space, a temperature sensor 70 and conducting wire 72 may be alternatively positioned within the suction lumen 20 itself, as illustrated in the detail cross-sectional view of FIG. 9. In this example, a temperature of the electrically conductive fluid recently in the immediate vicinity of the active screen electrode 40 and then aspirated into suction lumen 20 may be measured as one method for determining a temperature-effect induced in nearby tissues due to the electrosurgical procedure. Such temperature measurements could be used to control the RF output in order to provide therapies where it may be desirable to elevate the temperature of the target tissue to a specific temperature range. This configuration may also yield temperature data that may be used to directly correlate the temperature of the target tissue from the aspirated conductive fluid/irrigant and thereby allow the user to get direct feedback of the actual temperature of the tissue and/or limit the RF output depending on preset limits or for a given procedure or tissue type.

Figure 10:
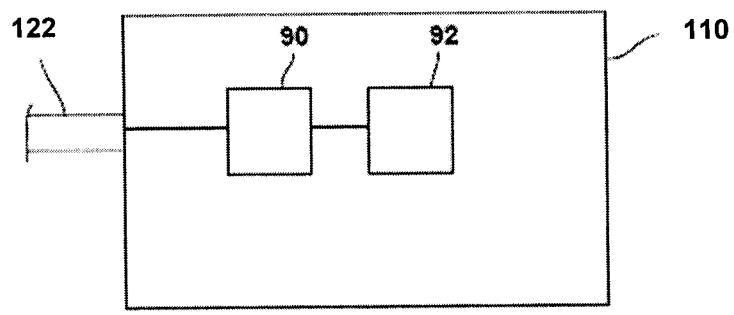
FIG. 10 is a schematic representation of a microcontroller within the controller which is coupled to the temperature sensor.

Independently from or in addition to the temperature sensing mechanisms in or along the probe 10, the power supply/controller 110 may also be configured for determining and/or controlling a fluid temperature within the body or joint space under treatment. FIG. 10 shows a representative schematic of controller 110 with cable 122 coupled thereto. The one or more conducting wires from their respective temperature sensors may be routed through cable 122 and into electrical communication with analog-to-digital (ADC) converter 90 which may convert the output of the temperature sensor to a digital value for communication with microcontroller 92. The measured and converted temperature value may be compared by microcontroller 92 to a predetermined temperature limit pre-programmed or stored within microcontroller 92 such that if the measured temperature value of the conductive fluid irrigating the body or joint space exceeds this predetermined limit, an alarm or indicator may be generated and/or the RF output may be disabled or reduced. Additionally and/or alternatively, the microcontroller 92 may be programmed to set a particular temperature limit depending upon the type of device that is coupled to controller 110.

Furthermore, microcontroller 92 may also be programmed to allow the user to select from specific tissue or procedure types, e.g., ablation of cartilage or coagulation of soft tissues, etc. Each particular tissue type and/or procedure may have a programmed temperature limit pre-set in advance depending upon the sensitivity of the particular anatomy to injury due to an elevation in temperature.

Figure 11:
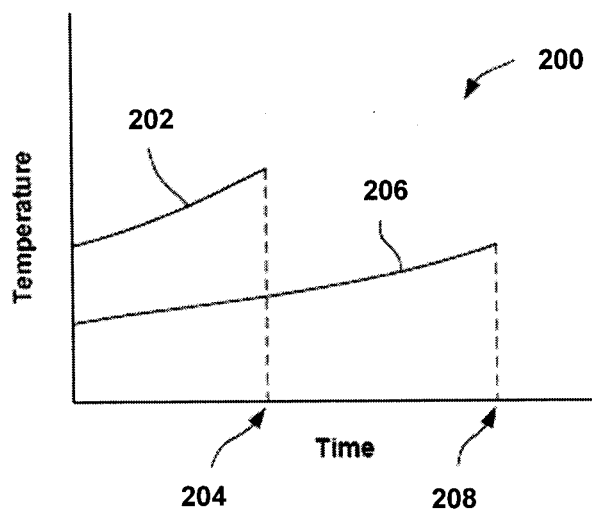
FIG. 11 is an illustrative graph showing how the microcontroller may be programmed comparing treatment time versus temperature.

In additional variations, the microcontroller 92 may be programmed to monitor the exposure of a body or joint space to a specific elevated fluid temperature level rather than limiting the treatment temperature upon the instantaneous measured temperature value. For example, as the fluid treatment temperature increases, tissue necrosis typically occurs more rapidly; thus, microcontroller 92 may be programmed to generate an alarm or indication based upon a combination of time-temperature exposure. An exemplary chart 200 is illustrated in FIG. 11 which shows first temperature plot 202 indicating treatment of a body or joint space exposed to a irrigating conductive fluid at a first elevated temperature level. Because of the relatively elevated fluid treatment temperature, the treatment time may be limited to a first predetermined time 204 by microcontroller 92 which may shut off or reduce the power level automatically. This is compared to second temperature plot 206 indicating treatment of a body or joint space exposed to a irrigating conductive fluid at a second elevated temperature level which is less than first temperature plot 202. Because of the lower relative temperature, tissue necrosis may occur at a relatively slower rate allowing the treatment time to be extended by microcontroller 92 to a relative longer time period to second predetermined time 208.

Figure 12:
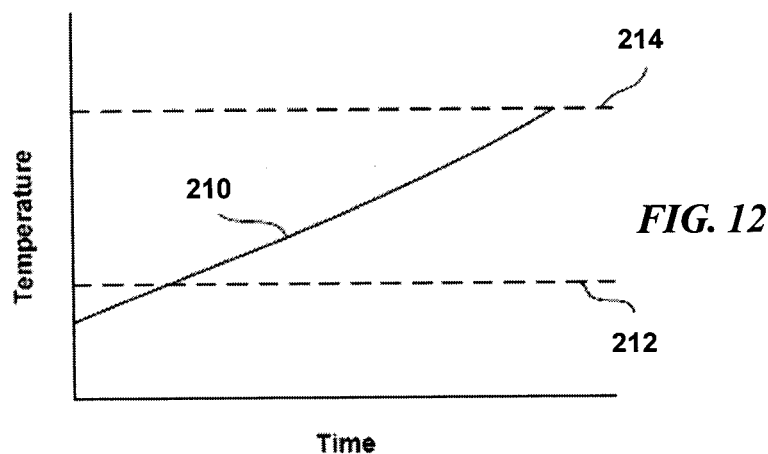
FIG. 12 is an illustrative graph showing how the microcontroller may be programmed to indicate an alarm at a first temperature threshold and to cease further power upon the temperature reaching a second temperature threshold.

In yet another variation, microcontroller 92 may be programmed to incorporate a set of multiple progressive temperature limits, as shown in the exemplary chart of FIG. 12. A first temperature limit 212 may be programmed whereby if the measured temperature rise 210 of the irrigating conductive fluid in the body or joint space exceeded first limit 212, an alarm or indication may be automatically generated by microcontroller 92 to alert the user. A second temperature limit 214 may also be programmed whereby if the measured temperature 210 of the irrigating conductive fluid in the body or joint space exceeded the second limit 214, microcontroller 92 may be programmed to reduce or deactivate the RF output of active electrode 12 to mitigate the risk of injury to the patient.

Figure 13:
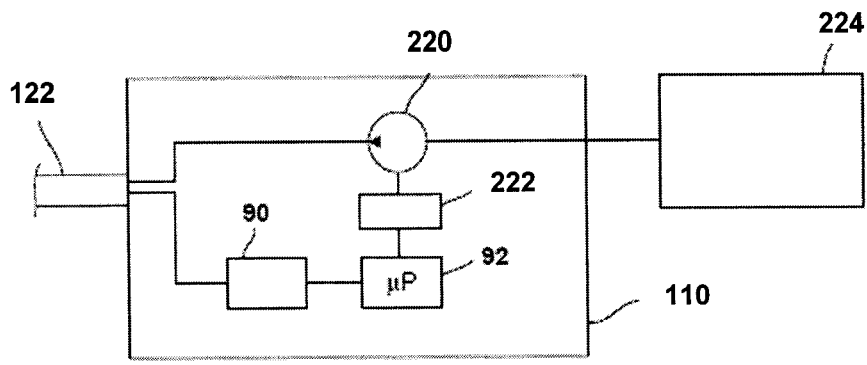
FIG. 13 is a schematic representation of a microcontroller and a fluid pump which may be used to control the inflow or outflow of fluids through an electrosurgical probe to control temperature.

Additionally and/or alternatively, controller 110 may be further configured to interface directly with a fluid pump, e.g., an arthroscopy saline pump 220 which provides a controlled in-flow of electrically conductive fluid (e.g., saline) to the body or joint space. Such a fluid pump 220 may be configured to provide control of both electrically conductive fluid in-flow to the body or joint space as well as out-flow from the body or joint space, as shown in the schematic illustration of FIG. 13. As illustrated, pump 220 may be electrically coupled to pump controller 222 which in turn may be in communication with microcontroller 92. Pump 220 may be further fluidly coupled to fluid reservoir 224 which holds the electrically conductive fluid and/or an empty reservoir (not shown) for receiving evacuated electrically conductive fluid from the body or joint space.

Figure 14A:
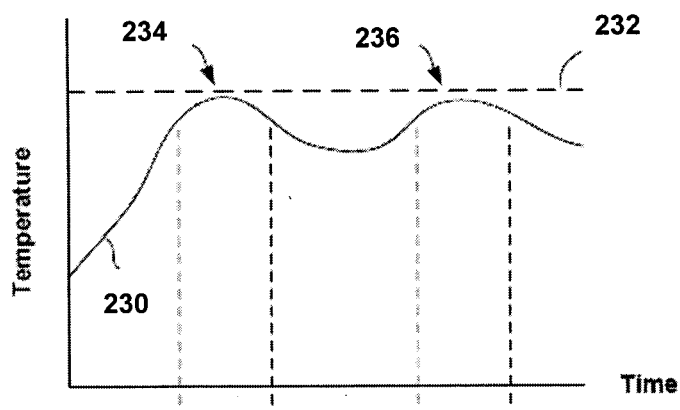
FIG. 14A is an illustrative graph showing measured temperature rise and decline as the flow rate of the fluid is varied.
Figure 14B:
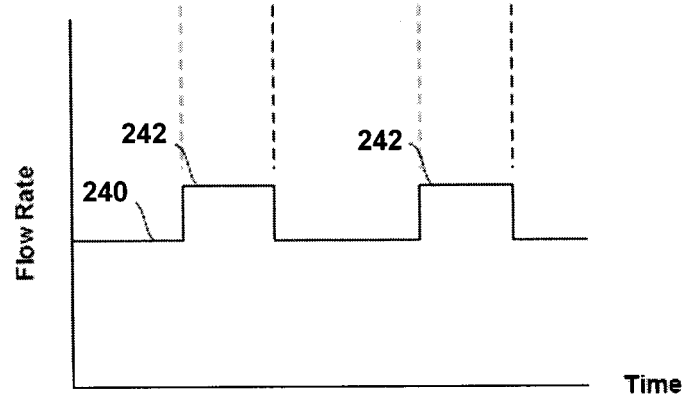
FIG. 14B is an illustrative graph showing increases in flow rate based upon the sensed temperature.

The measured temperature 230 of fluid within the body or joint space may be monitored and utilized as a control parameter for the fluid pump 220 whereby the fluid in-flow and/or out-flow may be regulated to maintain a temperature of the body or joint space within a specified range or below a temperature limit where potential injury could occur. An example of this is illustrated in the chart of FIG. 14A, which shows the measured temperature 230 of fluid within the body or joint space increasing towards a pre-programmed temperature limit 232. Once the measured temperature 230 has approached 234, 236 or exceeded this limit 232, the fluid pump 220 flow rate may be automatically increased by microcontroller 92 from a first pump flow rate 240 to a second increased flow rate 242 until the measured temperature 230 decreases, at which point the pump flow rate may be automatically decreased to the first pump flow rate 240, as indicated in FIG. 14B. This temperature moderation may be continued by cycling the flow rates between an initial level and an increased level for the duration of the procedure if so desired. Alternatively, the out-flow rate may be increased to remove any heated fluid to lower the temperature of fluid within the body or joint space.

Other modifications and variations can be made to the disclosed embodiments without departing from the subject invention. For example, other uses or applications are possible. Similarly, numerous other methods of controlling or characterizing instruments or otherwise treating tissue using electrosurgical probes will be apparent to the skilled artisan. Moreover, the instruments and methods described herein may be utilized in instruments for various regions of the body (e.g., shoulder, knee, etc.) and for other tissue treatment procedures (e.g., chondroplasty, menectomy, etc.). Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

While preferred embodiments of this invention have been shown and described, modifications thereof can be made by one skilled in the art without departing from the scope or teaching herein. The embodiments described herein are exemplary only and are not limiting. Because many varying and different embodiments may be made within the scope of the present teachings, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical method for monitoring temperature during an electrosurgical procedure to ablate soft tissue at a target site, the electrosurgical method comprising:

delivering high frequency energy to an active electrode terminal located at a distal end of an electrosurgical probe, said active electrode terminal being positioned in electrically conductive fluid during the electrosurgical procedure and wherein a current flow path from the active electrode terminal, through the electrically conductive fluid, to a return electrode is created when the high frequency energy is delivered;

monitoring a temperature signal indicative of a temperature of the electrically conductive fluid; and automatically suspending the delivering step for a suspension period while monitoring said temperature signal, wherein the suspension period is defined as a duration that continues until a rate of change in said temperature signal is less than a threshold value;

wherein the step of automatically suspending comprises suspending the delivery step for a plurality of suspension periods performed according to a suspension frequency (F) that is adjustable between 1 suspension period every 3 seconds and 2 suspension periods per second.

2. The method of claim 1 wherein said threshold value is 1 degree per 50 ms.

3. The method of claim 1 wherein said suspension period is at least 250 ms.

4. The method of claim 1 wherein said suspension frequency (F) is adjustable based on a power output.

5. The method of claim 1 wherein said suspension frequency (F) is adjustable based on receiving an input of a type of surgical procedure to be performed.

6. The method of claim 1 wherein said suspension frequency (F) is adjustable based on the temperature signal, and said suspension frequency (F) is increased once the temperature signal reaches a threshold limit.

7. The method of claim 1 further comprising: circulating the electrically conductive fluid to the target site at a flowrate; comparing the temperature signal to a desired temperature range; and adjusting the flowrate based on the temperature signal.

8. The method of claim 1 wherein said delivering step forms a plasma in a vicinity of the active electrode terminal.

9. The method of claim 1 wherein said target site is a joint.

10. The method of claim 1 wherein said automatically suspending step is performed by reducing a voltage difference between the active electrode terminal and the return electrode to less than 100 volts.

11. An electrosurgical method comprising:

delivering high frequency energy to an active electrode located at a distal end of an electrosurgical probe, said active electrode positioned in an electrically conductive fluid during an electrosurgical procedure, and wherein electrical current flows from the active electrode through the electrically conductive fluid to a return electrode when the high frequency energy is delivered; and automatically suspending the delivering step for a suspension period, during the suspension period monitoring a temperature signal, the temperature signal indicative of a temperature of the electrically conductive fluid; and wherein the suspending step comprises suspending the delivery step for a plurality of suspension periods performed according to a suspension frequency (F) that is adjustable between is at least 1 period every 3 seconds and less than 2 periods per second.

12. The method of claim 11 further comprising monitoring the temperature signal during delivering of the high frequency energy.

13. The method of claim 11 wherein said suspension period is defined as a duration spanning until a change in temperature signal versus time is less than 1 degree per 50 ms.

14. The method of claim 11 wherein the duration of the suspension period is at least 250 ms.

15. The method of claim 11 wherein said suspension frequency (F) is adjustable based on a power output.

16. The method of claim 11 wherein said suspension frequency (F) is determined based on receiving an input of a type of surgical procedure to be performed.

17. The method of claim 11 wherein said suspension frequency (F) is adjustable based on the temperature signal, and said suspension frequency (F) is increased once the temperature signal reaches a threshold limit.

18. The method of claim 11 further comprising:

circulating the electrically conductive fluid to a target site at a flowrate; and comparing the temperature signal to a predetermined temperature range; and adjusting the flowrate based on the temperature signal.

19. The method of claim 11 wherein delivering high frequency energy further comprises forming plasma in the vicinity of the active electrode.

20. The method of claim 11 wherein automatically suspending step comprises reducing a voltage difference between the active electrode and the return electrode to less than 100 volts.

* * * * *